United States Patent
Aubert et al.

(10) Patent No.: US 6,953,447 B2
(45) Date of Patent: Oct. 11, 2005

(54) PRE-FILLED SAFETY INJECTION DEVICE WITH INTEGRATED WASTE COLLECTOR

(75) Inventors: Christophe Aubert, Cudrefin (CH); Roland Cherif-Cheikh, Barcelona (ES)

(73) Assignee: Societe de Conseils de Recherches et d'Applications Scientifiques (S.C.R.A.S) (FR)

( * ) Notice: Subject to any disclaimer, the term of this patent is extended or adjusted under 35 U.S.C. 154(b) by 76 days.

(21) Appl. No.: 10/278,163

(22) Filed: Oct. 22, 2002

(65) Prior Publication Data

US 2004/0078005 A1 Apr. 22, 2004

(51) Int. Cl.[7] .......................... A61M 5/00; A61M 5/32; B65D 83/10
(52) U.S. Cl. ...................... 604/110; 604/197; 128/919; 206/365
(58) Field of Search .............................. 604/93.01, 110, 604/164.08, 181, 187, 192, 197, 218, 220; 128/919; 206/363, 364, 365

(56) References Cited

U.S. PATENT DOCUMENTS

| | | | | |
|---|---|---|---|---|
| 3,677,247 A | * | 7/1972 | Brown ........................ | 604/197 |
| 3,828,775 A | * | 8/1974 | Armel ......................... | 604/196 |
| 3,890,971 A | * | 6/1975 | Leeson et al. ............... | 604/110 |
| 5,171,220 A | * | 12/1992 | Morimoto .................... | 604/88 |
| 5,417,326 A | * | 5/1995 | Winer ......................... | 206/365 |
| 5,519,931 A | * | 5/1996 | Reich .......................... | 29/426.3 |
| 5,536,945 A | * | 7/1996 | Reich .......................... | 250/507.1 |
| 5,611,429 A | * | 3/1997 | Phillips ....................... | 206/365 |
| RE36,693 E | * | 5/2000 | Reich .......................... | 250/507.1 |
| 6,576,918 B1 | * | 6/2003 | Fu et al. ...................... | 250/507.1 |

* cited by examiner

*Primary Examiner*—Nicholas D. Lucchesi
*Assistant Examiner*—Mark K. Han
(74) *Attorney, Agent, or Firm*—Muserlian, Lucas and Mercanti

(57) ABSTRACT

The invention relates to a pre-filled injection device for injecting a liquid or semisolid composition into a subject, said injection device comprising:

a housing (1) containing at its distal end the liquid or semisolid composition (2), a plunger (3) arranged to slide within the housing (1) to which is affixed a plunger stick (7) extending longitudinally from the plunger to the outside of the housing (1), a hollow needle (4) affixed to the distal end of the housing (1), said needle (4) connecting the interior part of the housing (1) with the outside where it extends longitudinally, and an airtight needle shield (5) which protects said needle (4), characterized in that said device further comprises a cap (6) designed to fit around the housing's proximal end and to fully cover said plunger stick (7), said cap (6) both preventing its accidental pushing or breakage before use and being adapted to receive the injection device once the injection into the subject has been carried out.

10 Claims, 5 Drawing Sheets

PRE-FILLED SAFETY INJECTION DEVICE WITH INTEGRATED WASTE COLLECTOR

BACKGROUND OF THE INVENTION

The invention relates to a device for injecting a liquid or semisolid composition into a subject, which device integrates in its protecting cap a waste collector.

Waste syringes have always constituted a problem since they may carry infectious vectors.

A common solution of the art is to use a needle cutting system or a Luer-Lock needle discarding system. Other more sophisticated solutions include syringes with elements protecting the needles after injection. However, these syringes are often complex to use, and therefore necessitate training of the personnel.

A further desirable feature of injection devices is the fact that they can be integrated into Standard Operating Procedures of hospitals.

SUMMARY OF THE INVENTION

The invention provides a simple and inexpensive device for injecting a liquid or semisolid composition into a subject which includes the solution to this problem in so far as it integrates in its protecting cap (or cover) the waste collector.

This device works in accordance with all safety approaches and the protecting cap also serves as an integrity protection and control in soft packaging like aluminium pouches.

The invention therefore first relates to a pre-filled injection device for injecting a liquid or semisolid composition into a subject, said injection device comprising:

- a housing (1) containing at its distal end the liquid or semisolid composition (2),
- a plunger (3) arranged to slide within the housing (1) to which is affixed a plunger stick (7) extending longitudinally from the plunger to the outside of the housing (1),
- a hollow needle (4) affixed to the distal end of the housing (1), said needle (4) connecting the interior part of the housing (1) with the outside where it extends longitudinally, and
- an airtight needle shield (5) which protects said needle (4),
- characterized in that said device further comprises a cap (6) designed to fit around the housing's proximal end and to fully cover said plunger stick (7), said cap (6) both preventing its accidental pushing or breakage before use and being adapted to receive the injection device once the injection into the subject has been carried out.

According to a variant of the invention, the pre-filled injection device is such that the cap includes in its inner or outer face blocking means cooperating with means present on the outer or inner face of the housing of the injection device in order to ensure that when the injection device is put into the cap designed to fit around the housing (e.g. around the housing's proximal end), said cap blocks the injection device so that both can no more be separated from each other.

Preferably, the pre-filled injection device will further comprise a piece (8) that is affixed at the proximal end of the housing (1). Said piece (8), which leaves the distal end of the reservoir free of masking or possibly contaminant element (e.g. sticker glue or ink) in the composition area, can be designed to receive printed stickers (on which the product name, the volume, the dosage, etc. can be indicated).

In that case, according to a preferred variant, the pre-filled injection device will be such that the housing (1) includes at its proximal end a flange (9) cooperating with assembling means (10) of the piece (8) that is affixed at the proximal end of the housing (1), said cooperation ensuring that said housing (1) and said piece (8) hold tightly together. According to another preferred variant which may be combined with the previous one, the pre-filled injection device will be such that the cap (6) includes at its open end blocking means (11) cooperating with blocking means (12) of the piece (8) that is affixed at the proximal end of the housing (1), wherein said blocking means (11) can only be activated when said cover (6) is on said housing (1) and not when it is on plunger stick (7) and said cooperation ensures that said cap (6) and said piece (8) can no more be separated from each other once the injection device is fully introduced into the cap (6). In another preferred variant, the piece (8) that is affixed at the proximal end of the housing (1) may be part of the housing (1).

Alternatively, the piece (8) that is affixed at the proximal end of the housing (1) may be replaced by a corresponding piece affixed at the open end of the cap (6). Said piece may be part of the cap (6).

According to a further general variant of the injection device of the invention, the cap (6) will comprise a flange (13) which will assist in the grip of said cap (6) when inserting the injection device into it. Preferably, this flange (13) will be located at a place where it can cooperate with the piece (8) that is affixed at the proximal end of the housing (1) in order to afford stability to said cap (6) when it is in its initial location (protecting the plunger stick (7)). More preferably in the latter case, both the outline of said flange (13) and the outline of the inner part of said piece (8) will have a non-circular shape in order to provide increased stability; for example, said flange (13) and said inner part of said piece (8) will possess an elliptic or rectangular outline (most preferably an elliptic form).

Other improvements to the basic version of the invention device (which may constitute an alternative to the inclusion of a flange (13) as described above or can be used in addition thereto) include the case wherein the cap (6) is equipped with small transversal flanges (not shown in the drawings) on its outer face close to its open end in order to improve grip of said cap (6).

With regard to the materials used for making the different pieces of the injection device, these should be adapted to the use/function of each piece. In particular:

- the plunger will be made of an elastic or bendable material like natural rubber or synthetic rubber (notably polybromobutyl or polychlorobutyl);
- the plunger stick will preferably be made of a rigid material like plastic or metal, or, alternatively, of the same material as the plunger;
- the housing will be made of a rigid material like plastic or glass (and notably of plastic);
- the piece that is affixed at the proximal end of the housing will preferably be made of a rigid material like plastic or glass; and
- the cap designed to fit around the housing's proximal end and to fully cover the plunger stick will preferably be made of a rigid material like plastic.

Besides, the injection device of the instant invention may be packaged in a sealed aluminium or plastic bag, or, alternatively, in a blister.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described below. All publications, patents, patent applications, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF THE DRAWINGS

Eventually.

DETAILED DESCRIPTION

It is believed that one skilled in the art can, based on the description used herein, utilize the present invention to its fullest extent. The following specific embodiments are, therefore, to be construed as merely illustrative, and not limiting.

Figure 1:
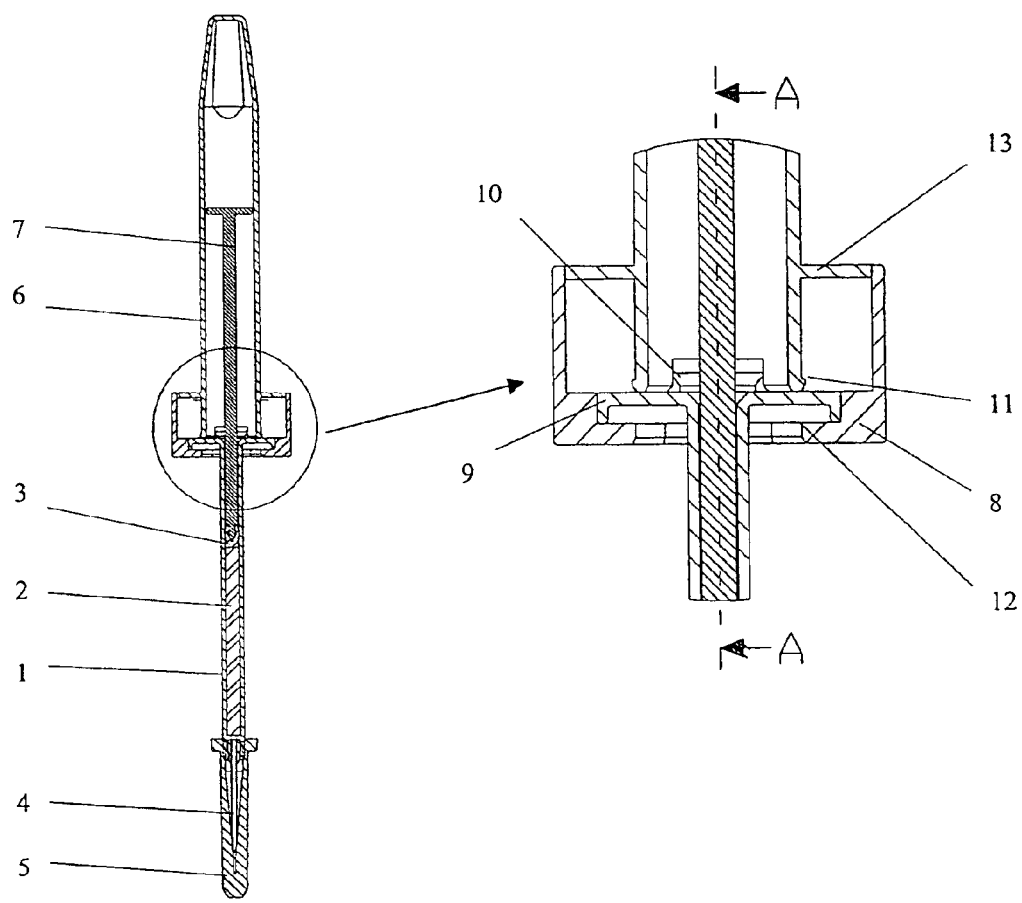
FIG. 1 is a cross-sectional view of an injection device with its waste cap according to the invention prior to use.

FIG. 1 shows an injection device comprising a housing 1 containing a liquid or semisolid composition 2. A plunger 3 is arranged to slide within the housing 1. At the distal end of the housing 1 is affixed a needle 4 which allows the communication between the inside of the housing 1 and the outside. This needle is covered by an airtight needle shield 5. To the plunger 3 is affixed a plunger stick 7 which extends longitudinally from the plunger 3 to the outside of the housing 1. A protection/waste cap 6 is covering the proximal end of the injection device, preventing accidental pushing of the plunger stick 7.

In the zoomed-in part of FIG. 1 is shown in detail the construction of the open end of the cap 6, of the proximal end the housing 1 and of a piece 8 that is affixed at the proximal end of the housing 1. Said piece 8 may be used for receiving stickers giving indication on the liquid or semisolid composition 2, but its main functions are to stabilize the cap 6 and to block said cap 6 after use of the injection device (for this particular feature, see also FIG. 4 and related description). The cap 6 rests on a flange 9 of the housing 1. The piece 8 is tightly affixed to the housing 1 by assembling means 10 (which can be better seen in FIG. 2).

Figure 2:
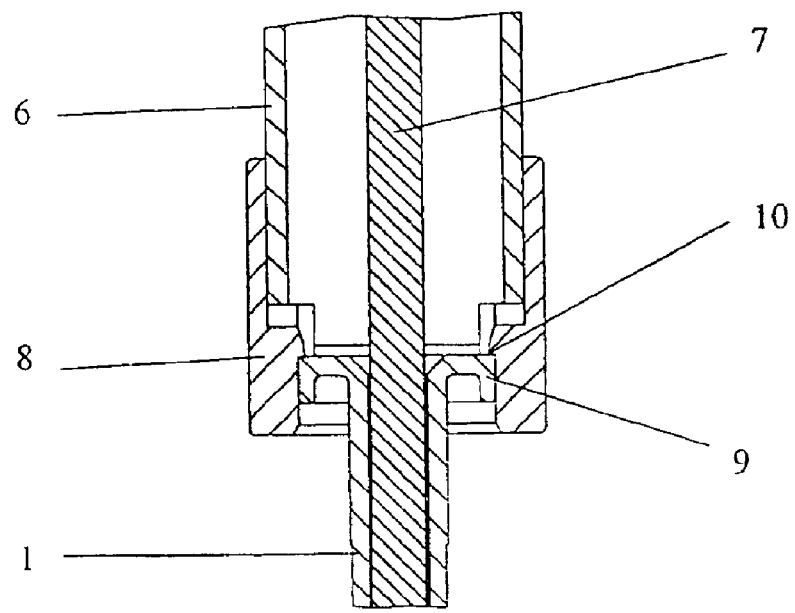
FIG. 2 is a cross-sectional view of the injection device of FIG. 1 along the AA plan viewed in the direction of the arrows of said FIG. 1.

FIG. 2 shows a transversal cross-sectional view of the device represented in FIG. 1 along the AA plan, this view being seen in the direction of the arrows of said FIG. 1. From this view, one can notice the assembling means 10 which solidarize the piece 8 with the housing 1 and the cap 6 which protects the plunger stick 7 from accidental pushing before actual injection. Said cap 6, which rests on the flange 9 of the housing 1, has a design that perfectly fits with the outline of the assembling means 10 of the piece 8.

Figure 3:
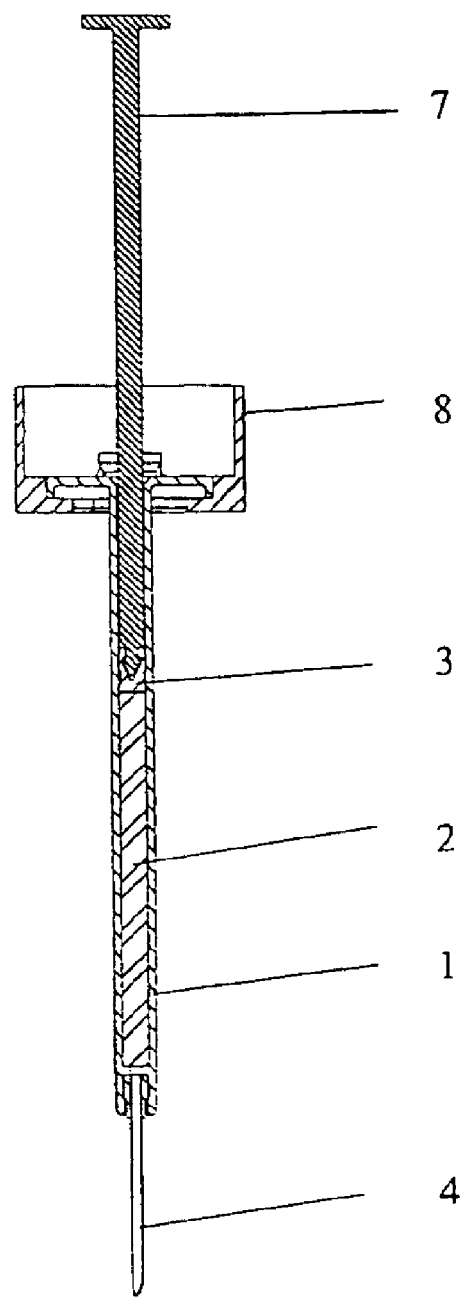
FIG. 3 is a cross-sectional view of the injection device of FIG. 1, the needle shield of which has been discarded and the protection/waste cap set aside.

FIG. 3 shows the injection device of FIG. 1 from which the needle shield 5 of the needle 4 has been discarded and the protection/waste cap has been set aside. The plunger stick 7 can now be pushed and the injection of the composition 2 contained in the distal end of the housing 1 carried out by action of the plunger 3.

Figure 4:
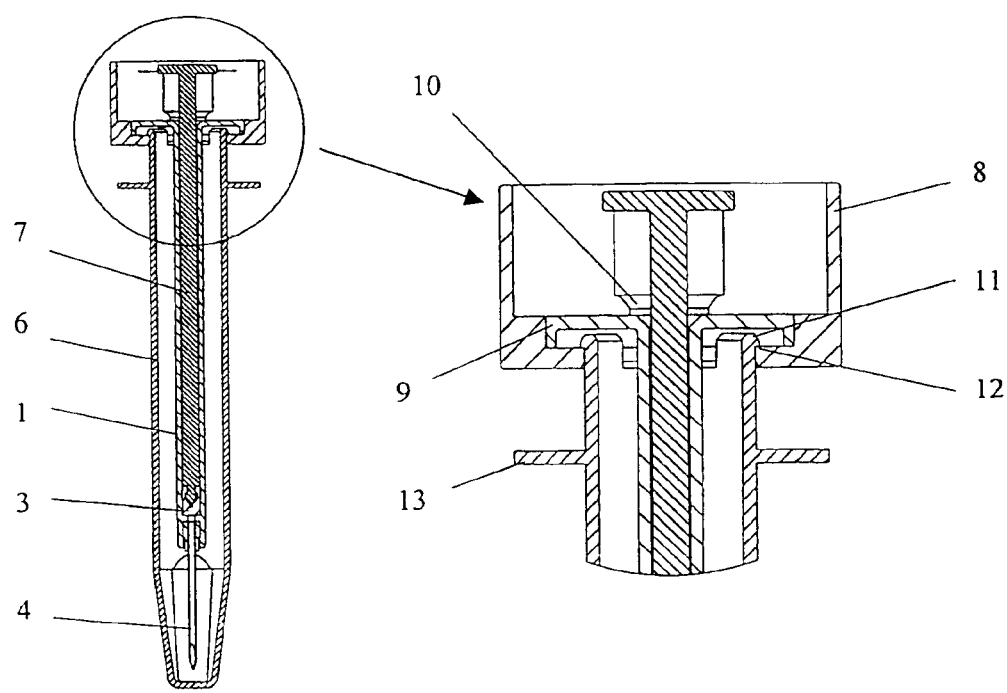
FIG. 4 is a cross-sectional view of the injection device of FIG. 1 after injection and insertion of the injection device into the protection/waste cap.

FIG. 4 shows how the injection device of FIG. 3 can be blocked in the protection/waste cap 6 of FIG. 1. The injection device, the plunger stick 7 of which has pushed the plunger 3 to its final position at the distal end of the housing 1, close to or touching the proximal end of needle 4, has been irreversibly inserted into the cap 6.

In the zoomed-in part of FIG. 4, one can notice that the blocking means 11 at the open end of the cap 6 imprison the cooperating means 12 of the piece 8 under the flange 9 of the housing 1 whereas the flange 13 can be used for assisting the blocking of the injection device by the cap 6, ensuring a better grip of the latter.

Figure 5:
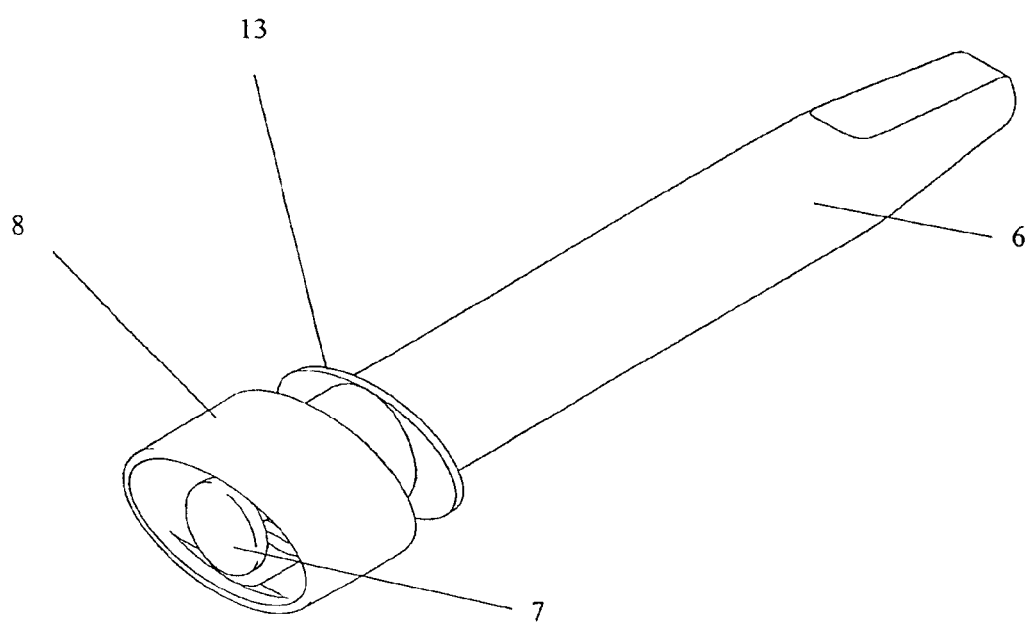
FIG. 5 is a three-dimensional view of an injection device according to the invention inserted in its protection/waste cap.

Eventually, FIG. 5 shows a three-dimensional view of the injection device after its insertion and blocking into the cap 6. The only pieces in contact with the outside are the cap 6 with its flange 13, the piece 8 and the proximal end of the plunger stick 7, so that no injury through the device can occur for the manipulator at this stage.

OTHER EMBODIMENTS

It is to be understood that while the invention has been described in conjunction with the detailed description thereof, the foregoing description is intended to illustrate and not limit the scope of the appended claims. Other aspects, advantages, and modifications are within the claims.

What is claimed is:

1. A pre-filled injection device for injecting a liquid or semisolid composition into a subject, said injection device comprising:
    a housing (1) containing at its distal end the liquid or semisolid composition (2) to be injected,
    a plunger (3) arranged to slide within the housing (1) to which is affixed a plunger stick (7) extending longitudinally from the plunger to the outside of the housing (1),
    a hollow needle (4) affixed to the distal end of the housing (1), said needle (4) connecting the interior part of the housing (1) with the outside where it extends longitudinally, and an airtight needle shield (5) which protects said needle (4),
    wherein said device further comprises a cap (6) designed to fit around the housing's proximal end and to fully cover said plunger stick (7), said cap (6) both preventing its accidental pushing or breakage before use and being adapted to receive the injection device one the injection into the subject has been carried out, the cap includes in its inner or outer face a blocking element cooperating with an element present on the outer or inner face of the housing of the injection device to ensure that when the injection device is put into the cap designed to fit around the housing, said cap blocks the injection device so that both can no more be separated from each other.

2. The pre-filled injection device of claim 1 which further comprises a piece (8) that is affixed at the proximal end of the housing (1) and is designed to receive printed stickers.

3. The pre-filled injection device of claim 1 wherein the housing (1) includes at its proximal end a flange (9) cooperating with assembling element (10) of the piece (8) that is affixed at the proximal end of the housing (1), said cooperation ensuring that said housing (1) and said piece (8) hold tightly together.

4. The pre-filled injection device of claim 1 which further comprises a piece that is affixed at the open end of the cap and is designed to receive printed stickers.

5. The pre-filled injection device of claim 4 wherein the piece that is affixed on the cap and that is designed to receive printed stickers is part of the cap.

6. The pre-filled injection device of claim 1 wherein the cap (6) comprises a flange (13) which will assist in the grip of said cap (6) when inserting the injection device into it.

7. The pre-filled injection device of claim 6 wherein the flange (13) is located at a place where it can cooperate with the piece (8) that is affixed at the proximal end of the housing (1) to afford stability to the cap (6) when it is in its initial location.

8. The pre-filled injection device of claim 1 wherein the cap (6) is equipped with small transversal flanges on its outer face close to its open end to improve grip of said cap (6).

9. A pre-filled injection device for injecting a liquid or semisolid composition into a subject, said injection device comprising:

a housing (1) containing at its distal end the liquid or semisolid composition (2) to be injected, a plunger (3) arranged to slide within the housing (1) to which is affixed a plunger stick (7) extending longitudinally from the plunger to the outside of the housing (1), a hollow needle (4) affixed to the distal end of the housing (1) said needle (4) connecting the interior part of the housing (1) with the outside where it extends longitudinally, and an airtight needle shield (5) which protects said needle (4), wherein said device further comprises a cap (6) designed to fit around the housing's proximal end and to fully cover said plunger stick (7), said cap (6) both preventing its accidental pushing or breakage before use and being adapted to receive the injection device once the injection into the subject has been carried out, a piece (8) that is affixed at the proximal end of the housing (1), the cap (6) includes at its open end a blocking element (11) cooperating with blocking element (12) of the piece (8) that is affixed at the proximal end of the housing (1), wherein said blocking element (11) can only be activated when said cover (6) is on said housing (1) and not when it is on plunger stick (7) and said cooperation ensures that said cap (6) and said piece (8) can no more be separated from each other once the injection device is fully into the cap (6).

10. The pre-filled injection device of claim 9 wherein the piece that is affixed at the proximal end of the housing and is designed to receive printed stickers is part of the housing.

* * * * *